United States Patent [19]

Lyons

[11] Patent Number: 4,933,669
[45] Date of Patent: Jun. 12, 1990

[54] AEROSOL, VAPOR AND LIQUID CHEMICAL AGENT DETECTOR WITH EXTENDING SENSOR PLATE

[75] Inventor: Robert C. Lyons, Aberdeen, Md.

[73] Assignee: The United States of America as represented by the Secretary of the Army, Washington, D.C.

[21] Appl. No.: 392,865

[22] Filed: Aug. 11, 1989

[51] Int. Cl.$^5$ .............................................. G08B 17/10
[52] U.S. Cl. ................................... 340/632; 73/29.01
[58] Field of Search ............................... 340/632–634; 73/27 R, 27 A, 28, 26, 29, 23

[56] References Cited

U.S. PATENT DOCUMENTS

| | | | |
|---|---|---|---|
| H454 | 4/1988 | Sickenberger et al. | 73/27 R |
| 3,445,669 | 5/1969 | Jordan et al. | 340/632 |
| 4,216,468 | 8/1980 | Kaufmann | 340/628 |
| 4,231,249 | 11/1980 | Zuckerman | 340/632 |
| 4,297,689 | 10/1981 | Shaw et al. | 340/632 |
| 4,525,704 | 6/1985 | Campbell et al. | 340/632 |
| 4,542,541 | 9/1985 | Eyler | 73/26 |
| 4,599,609 | 7/1986 | Blanchard | 340/632 |
| 4,668,940 | 5/1987 | Beard et al. | 340/632 |
| 4,841,282 | 6/1989 | Reis | 340/628 |

FOREIGN PATENT DOCUMENTS

| | | | |
|---|---|---|---|
| 0888322 | 8/1953 | Fed. Rep. of Germany | 340/632 |
| 2137389 | 10/1984 | United Kingdom | 340/632 |

Primary Examiner—Joseph A. Orsino
Assistant Examiner—Jill Jackson
Attorney, Agent, or Firm—Anthony T. Lane; Edward Goldberg; Michael C. Sachs

[57] ABSTRACT

A chemical agent detector having a pair of vapor/aerosol chemical agent detector cells mounted with a lithium battery in a detection cell module. A liquid agent detector having a hinged plate is attached to an electronic system which includes a signal processor that energizes a plurality of warning LED's and a horn in response to energization of selected agent detectors. An air pump is mounted on the housing for the electronics to force air across the detection cells. The detection cell module is connected to the housing for the electronics. A battery compartment is connected to the detection cell module and includes means for permitting an external power source to be connected thereto.

9 Claims, 3 Drawing Sheets

AEROSOL, VAPOR AND LIQUID CHEMICAL AGENT DETECTOR WITH EXTENDING SENSOR PLATE

The invention described herein may be manufactured, used, and licensed by or for the Government for governmental purposes without the payment to me of any royalty thereon.

BACKGROUND OF THE INVENTION

1. Field of the Invention

The present invention relates generally to a chemical agent detector and, more specifically, to a device for use in the early detection and warning of the presence of an aerosol, vapor, and/or liquid droplet chemical agent.

2. Description of the Prior Art

Those concerned with the development of chemical agent detectors have long recognized the need for a reliable agent detector capable of detecting the presence of chemical agents in both vapor and droplet form. For example, U.S. Pat. No. 4,542,641 discloses an improved chemical agent detector that includes a droplet collector assembly having an air permeable surface for intercepting falling droplets and causing the droplets to vaporize into a sample airstream which is led through an inlet of a vapor sensor for detection. Numerous other types of chemical agent detectors and alarms have been developed and made available for sensing one or more of the known chemical agents currently in use. Although a number of such devices have been developed and proposed, there are primarily only three automatic detection and alarm devices available to the combat soldier today. The M8 and M8A1 alarms are used by the Army and Marines. The IDS alarm is used by the Air Force and Navy.

Although there has been a long recognized need for improvements in several alarm features, no practical device has yet been devised that resolves many of the current shortcomings. For example, some devices do not have the capability of performing multi-agent detection. Others do not have the ability of interfacing with remote warning systems. Still others do not have a self-test capability. Many require routine maintenance services for continuous operation while some have limited battery life. A number of alarms have excess size and weight. More important, most do not have the capability of detecting chemical agents in the aerosol, vapor and liquid form in a single device.

Consequently, because of these and other deficiencies, those skilled in these arts recognize the need for an improved chemical agent alarm that mitigates the many problems resulting from these deficiencies. The present invention fulfills this need.

SUMMARY OF THE INVENTION

It is, therefore, an object of the present invention to provide an improved chemical agent detection and alarm system that in a single device is capable of detecting chemical agents in the aerosol, vapor and liquid form.

Another object is to provide a detector and alarm capable of performing multi-agent detection.

A further object of the invention is to provide a chemical agent detector and alarm that can interface with remote warning systems.

A still further object is to provide a chemical agent detector and alarm with a self-test feature.

Yet another object of the present invention is the provision of a chemical agent detector and alarm that requires limited maintenance service, is miniaturized, is light-weight and requires minimum power for operation.

To attain this, the present invention contemplates a chemical agent detector having a pair of vapor/aerosol chemical agent detector cells mounted with a lithium battery in a detection cell module.

A liquid agent detector having a hinged plate is attached to an electronic system which includes a signal processor that energizes a plurality of warning LED's and a horn in response to energization of selected agent detectors. An airpump is mounted on the housing for the electronics to force air across the detection cells. The detection cell module is connected to the housing for the electronics. A battery compartment is connected to the detection cell module and includes means for permitting an external power source to be connected thereto.

These features and other objects of the invention will be more fully understood by reference to the following drawings and detailed description of the preferred embodiment.

BRIEF DESCRIPTION OF THE PREFERRED EMBODIMENT

DETAILED DESCRIPTION OF THE PREFERRED EMBODIMENT

Figure 1:
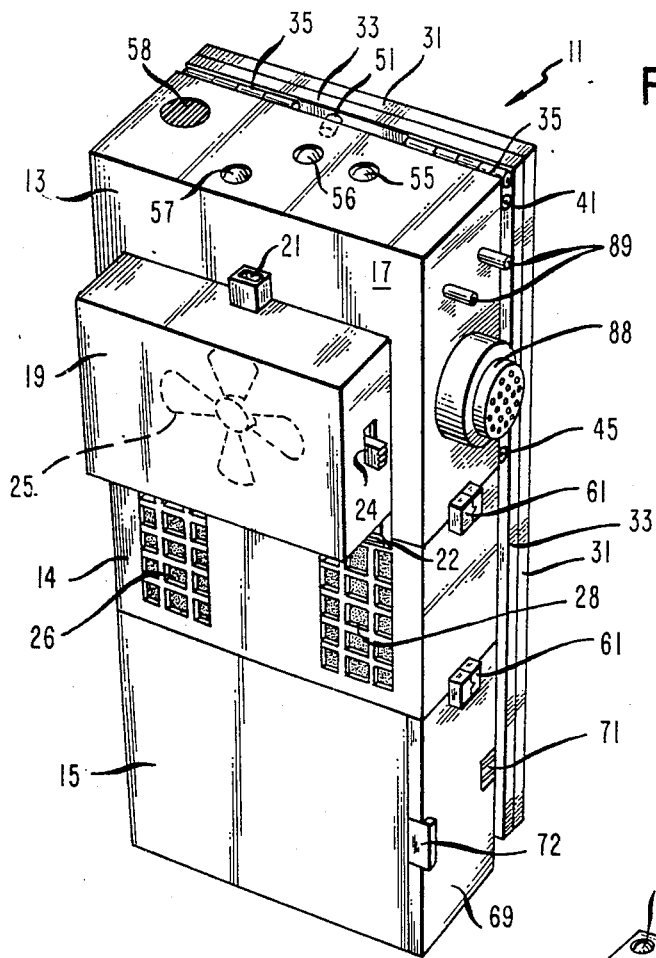
FIG. 1 is a pictoral view of the preferred embodiment.

Referring now to the drawings wherein like reference characters represent like parts throughout the several views, there is shown a chemical agent detection apparatus 11 made up of an electronics/liquid detection module 13, detector cells module 14 and a battery compartment 15. These items are joined to each other by tabs 61 to form a generally rectangular-shaped box that may be held in the hand or carried in the pocket of the user.

The electronics/liquid detection module 13 includes a housing 17 that has a forced-air system 19 mounted on the front face thereof. System 19 includes an air inlet orifice 21 at its upper end and spaced forced-air outlet orifices 22 and 23 on the bottom portion. An on-off switch 24 is mounted on the side surface of system 19.

Figure 3:
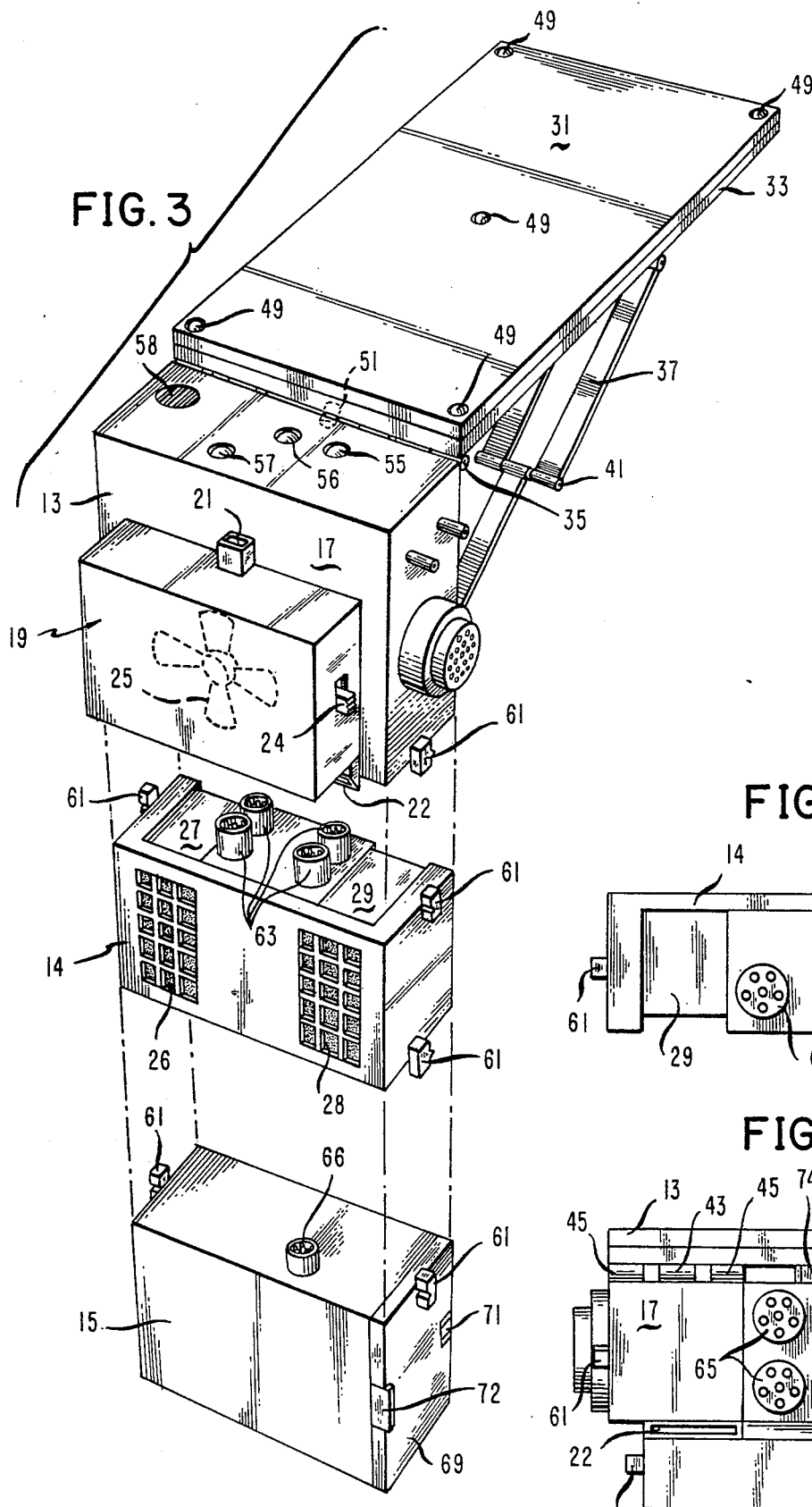
FIG. 3 is an exploded, pictoral view similar to the view shown in FIG. 1.
Figure 4:
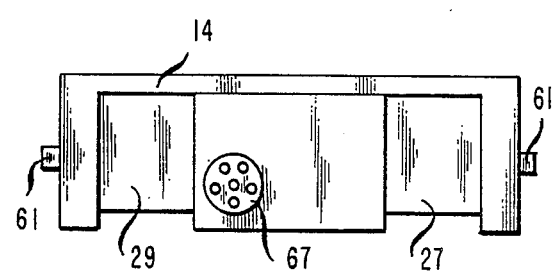
FIG. 4 is a bottom view of a portion of the preferred embodiment.

System 19 includes a conventional forced-air device such as a fan or air pump 25 shown diagrammatically in FIGS. 1 and 3. The forced air system 19 provides vaporization and enhanced diffusion of gaseous chemical agents across the front diffusion screens 26 and 28 of detection cells 27 and 29, respectively, in module 14. The on-off switch 24 provides user control to operate the air pump 25. Power for the air pump 25 is derived from a battery pack 16 contained in compartment 15.

A liquid agent detection plate 31 is superimposed on a mounting plate 33 that is hinged to the rear surface of module 13 by a pair of hinges 35. A folding bracket 37 has a plurality of hinged arms that are hinged to each other by a center hinge 41, to the module 13 by hinge 43 and to the mounting plate 33 by hinges 45.

Figure 2:
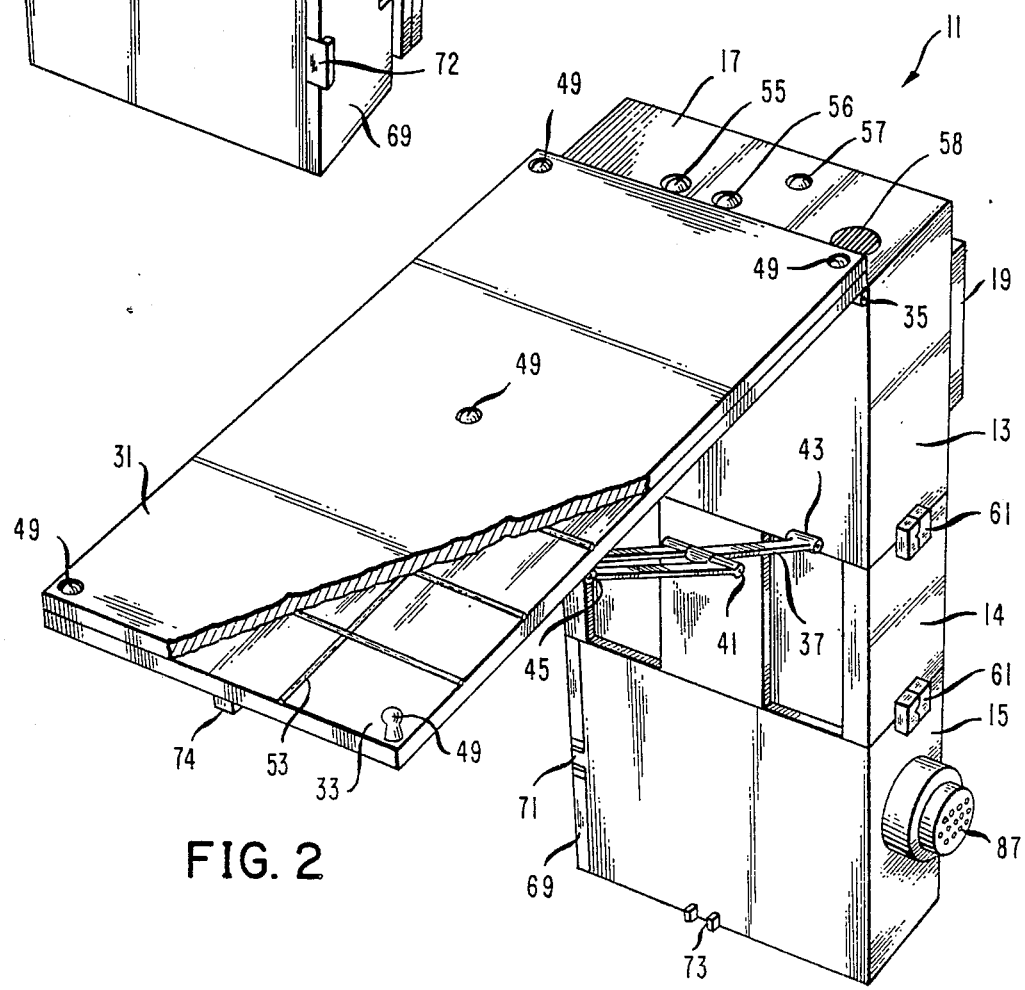
FIG. 2 is a pictoral view of the device shown in FIG. 1 with the liquid agent detector extended.

As seen in FIG. 2, the inside surface of detection plate 33 has four corner and one center contact mounting posts 49. Posts 49 protrude from the surface of plate 33 to mate with openings similarly placed on the plate 31. Posts 49 are electrically conductive and as such, in addition to supporting the removable plate 31, they make electrical contact with plate 31. An electronic circuit, to be described in detail below, is located in housing 17 and has a flexible cable 51 with a plurality of conductors therein that are connected to posts 49 via the interior of plate 33.

A grid of electrical heating elements 53 are located on the surface of plate 33. Heating elements 53 are connected to the electronic circuit in housing 17 via cable 51.

Three light-emitting diodes (LED) 55, 56, 57 extend through openings on the upper surface of housing 17. An audio warning device, such the a beeper or horn 58, is also located on the upper surface of housing 17.

Figure 5:
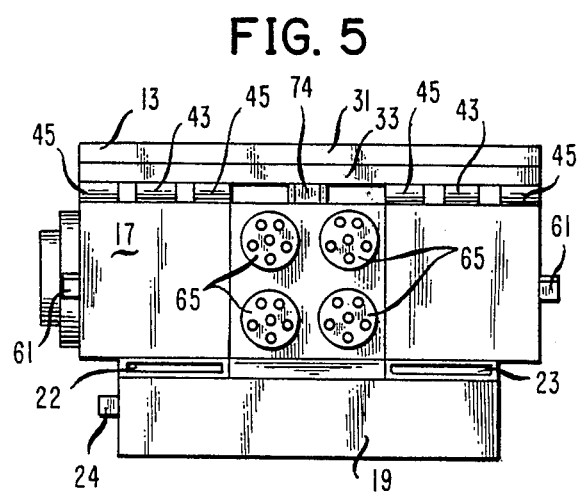
FIG. 5 is a bottom view of another portion of the preferred embodiment.

The module 14 is removably connected to the bottom surface of housing 17 by locking tabs 61. The upper surface of module 14 has four male connectors 63 (FIG. 3) which mate with four female connectors 65 (FIG. 5) that are similarly located on the bottom surface of housing 17.

Figure 6:
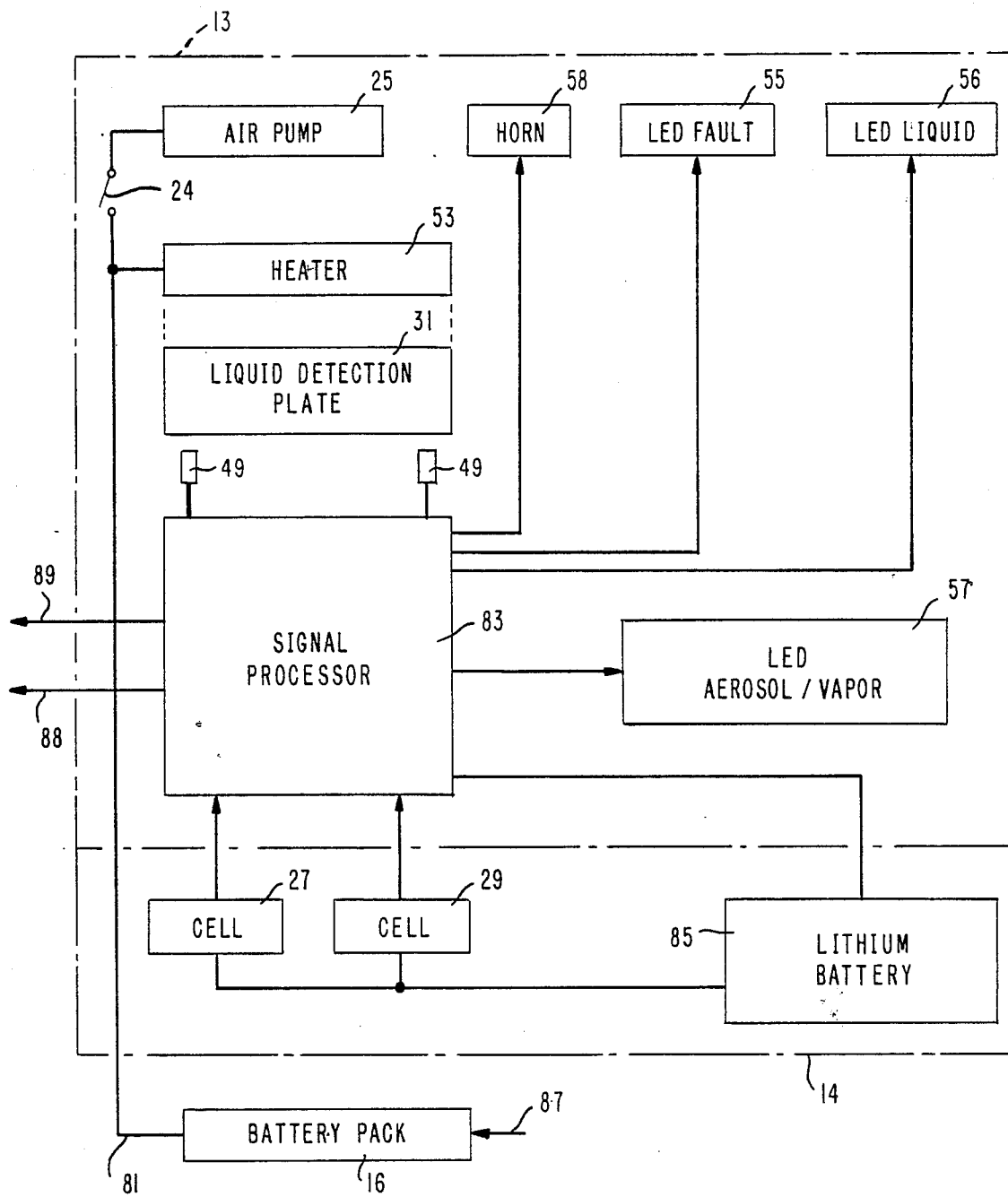
FIG. 6 is a functional block diagram of the major electronic components of the preferred embodiment.

Battery compartment 15 also has locking tabs 61 for mating with similarly placed tabs 61 on module 14. A male connector 66 on the upper surface of compartment 15 mates with a female connector 67 extending from the bottom surface of module 14. Compartment 15 has a hinged door 69, with a hinge 71 and a latch 72, that permits access thereto for placement of a DC battery pack 16 (FIG. 6). At the bottom edge on the rear of the compartment 15, there is a connector 73 (FIG. 2) that mates with a connector 74 at the bottom, inside edge of plate 33 for locking the plate 33 in the closed position (FIG. 1).

With particular reference to FIG. 6, the operation of the apparatus 11 will now be described. The battery pack 16 has a DC power line 81 that supplies power to the heater element 53 and the air pump 25. Power is conducted from the battery pack 16 via connectors 66, 67, module 14, and connectors 63, 65 to housing 17.

The heater elements 53 will provide sufficient heat to plate 31 to warm liquid agent droplets that may impinge thereon from the surrounding atmosphere. The liquid agent detector plate 31 may be selected from any of the commercially available devices. A typical plate 31 may consist of a conductive paint having as primary components resin, carbon, and silver. When a liquid droplet of chemical agent impacts on the detection plate 31, an increase of the electrical resistance of the paint is caused by the swelling of the silver. This resistance is detected by a signal processor 83 (FIG. 6) via conductive posts 49. A typical liquid detector 31 can detect such chemical agents as nerve agent Soman, commonly referred to as GD, nerve (VX) and blister (HD, L).

It is noted that the battery pack 16 preferably supplies power to only the heater elements 53 and the air pump 25. Power for operating the remaining elelctronic components is derived from lithium battery 85 housed in module 14 as shown in FIG. 6.

Cells 27 and 29, connected to battery 85, are preferably electrochemical cells having electrolites that collect chemical agents that diffuse into the cells 27, 29, either with or without help from air pump 15. The output of cells 27, 29 will be a measure of the chemical agent concentrations in the electrolite. The cells 27, 29 preferably detect nerve, blister, blood (AC, CK) and choking chemical warfare agents in the aerosol/vapor state. When a threshold level is reached in the output of either cells 27 or 29 or plate 31, the signal processor 83 will energize the appropriate visual warning devices, i.e. LED 55 and horn 58.

It may be desirable at times to place the apparatus 11 at some remote point with a conventional warning device connected thereto. For this purpose output terminals 89 extend from the housing 17. The signal processor 83 will provide an appropriate output signal at terminals 89 when a chemical agent has been detected. This output signal will be available to energize a remote warning device having conductors connected to terminals 89. Additionally, a communications port 88 is also provided for connection to a conventional communication device such as a radio (not shown). The battery pack 16 has an input terminal 87 for connection to an external DC power source such as a motor vehicle battery. The battery pack 16 may typically include three 9-volt batteries in parallel. A conventional converter may also be part of pack 16 so that an external 24-volt source may be connected thereto at terminal 87.

In a typical situation, the apparatus 11 is assembled and used with the bracket 37 extended and locked in the position shown in FIG. 2. Falling liquid droplets of a chemical agent are intercepted by the heated plate 31 thereby causing a change in resistance of the plate 31 where the liquid droplets impacted plate 31. As such, the electrical current distribution across plate 31 will change appreciably thereby causing the currents at conductive posts 49 to change in a manner that may be detected by signal processor 83 which in turn energizes LED 56 and horn 58.

When the on-off switch 24 is in the "On" position, chemical vapors and aerosols in the atmosphere will be drawn into orifice 21 and forced to cross screens 26, 28 via orifices 22, 23 by air pump 25. Such chemical agents will be diffused into cells 27, 29 causing electrochemical action to take place therein. This action will be detected by signal processor 83 which will respond by energizing horn 58 and LED 56. The LED 57 will be energized by signal processor 83 when an improper voltage or current condition occurs in signal processor 83. The present apparatus 11 has improved sensitivity because the detector cells 27, 29 are supplied with air from the air pump 25. Also, apparatus 11 is more versatile because both liquid droplet agent detection and aerosol/vapor detection are possible simultaneously in a single unit. Additionally, there are a plurality of warning devices that will distinguish which type of agent has been detected. Remote warning, provided by the communication device and/or remote warning terminals 89, renders the apparatus 11 more accessable. Also, there is less maintenance because the lithium battery 85 will provide long-term power.

Obviously many modifications and variations of the present invention are possible in the light of the above teachings. For example, the apparatus 11 may be used effectively without energizing the heater 53 or operating the air pump 25. As such, it is not necessary for battery pack 16 in battery compartment 15 to have a full charge or to be assembled in order for the apparatus 11 to operate. Because the apparatus 11 is modular, it may be conveniently upgraded by substituting new components. Additionally, the apparatus 11 may be designed to incorporate a droplet collector assembly which includes an air permiable surface disposed to intercept falling droplets and adapted to cause vaporization of the intercepted droplets into the air pump 25 drawn through the surface member. It is, therefore, to be understood, that within the scope of the appended claims, the invention may be practiced otherwise than as specifically described.

What is claimed is:

1. A chemical agent detector comprising:

a housing;

a liquid agent detector unit pivotally connected to said housing; wherein said detector unit includes a flat plate and a hinged bracket joined to said flat plate and said housing for holding said plate in a position extending from said housing; and an aerosol/vapor chemical agent detector module removably joined to the housing; and a battery compartment removably joined to said detector module.

2. The detector of claim 1 wherein said detector module includes at least one aerosol/vapor detector cell having a diffusion screen mounted thereon.

3. The detector of claim 2 further including a forced air means mounted on said housing for forcing air across said screen.

4. The detector of claim 3 further including a battery mounted in said battery compartment for providing electrical power to said cell.

5. The detector of claim 4 wherein said module includes a plurality of aerosol/vapor detector cells.

6. The detector of claim 5 further including output terminal means for connection to a remote warning device.

7. The detector of claim 6 further including audio warning means mounted on said housing for sounding an audio alarm when an agent is detected.

8. The detector in accordance with claim 7 further including lights mounted on said housing for providing a visual warning when an agent has been detected.

9. The detector in accordance with claim 8 wherein a plurality of lighting means are provided on said housing for providing a warning for the detection of different agents.

* * * * *